United States Patent
Roy Trudel et al.

(10) Patent No.: US 8,836,523 B2
(45) Date of Patent: Sep. 16, 2014

(54) FAULT GAS ALARM SYSTEM

(75) Inventors: Anik Roy Trudel, Montreal (CA);
Mariana Barbulescu, Dollard-des-Ormeaux (CA); Yong Ng Tong, Dollard-des-Ormeaux (CA)

(73) Assignee: General Electric Company, Schenectady, NY (US)

( * ) Notice: Subject to any disclaimer, the term of this patent is extended or adjusted under 35 U.S.C. 154(b) by 433 days.

(21) Appl. No.: 13/112,469

(22) Filed: May 20, 2011

(65) Prior Publication Data

US 2012/0293333 A1    Nov. 22, 2012

(51) Int. Cl.
| | | |
|---|---|---|
| *G08B 17/10* | (2006.01) | |
| *H01H 9/00* | (2006.01) | |
| *G01N 7/00* | (2006.01) | |
| *G01N 1/22* | (2006.01) | |
| *G01N 33/26* | (2006.01) | |
| *G01N 30/02* | (2006.01) | |
| *H01S 3/00* | (2006.01) | |
| *G01N 31/00* | (2006.01) | |
| *G06F 11/30* | (2006.01) | |
| *G06F 11/00* | (2006.01) | |
| *G08B 25/00* | (2006.01) | |
| *H01F 29/04* | (2006.01) | |
| *G08B 21/18* | (2006.01) | |
| *H01F 27/14* | (2006.01) | |

(52) U.S. Cl.
CPC .......... *H01H 9/0005* (2013.01); *G08B 25/002* (2013.01); *H01F 29/04* (2013.01); *G08B 21/182* (2013.01); *H01F 27/14* (2013.01); *H01H 2009/0061* (2013.01)
USPC .......... 340/632; 702/24; 702/183; 702/188; 73/19.01; 73/19.12; 73/19.11; 73/19.02; 359/341.1

(58) Field of Classification Search
USPC ...................... 340/632, 635; 702/24
See application file for complete search history.

(56) References Cited

U.S. PATENT DOCUMENTS

| | | | | |
|---|---|---|---|---|
| 4,236,404 | A | * | 12/1980 | Ketchum et al. ............. 73/19.02 |
| 4,271,474 | A | | 6/1981 | Belanger et al. |
| 4,402,211 | A | * | 9/1983 | Sugawara et al. ............ 73/19.11 |
| 4,654,806 | A | * | 3/1987 | Poyser et al. ................. 700/292 |
| 4,890,478 | A | * | 1/1990 | Claiborne et al. ........... 73/19.11 |
| 5,127,962 | A | * | 7/1992 | Inoue et al. ................ 134/22.12 |

(Continued)

FOREIGN PATENT DOCUMENTS

EP    1 470 948 A1    10/2004

OTHER PUBLICATIONS

U.S. Appl. No. 13/112,424, filed May 20, 2011, Notice of Allowance and Fees Due dated Dec. 18, 2013.

(Continued)

*Primary Examiner* — Jack K Wang
(74) *Attorney, Agent, or Firm* — Hoffman Warnick LLC; William Heinze

(57) ABSTRACT

A fault gas alarm system is disclosed. In one embodiment, the fault gas alarm system includes: a gas sensor configured to fluidly connect with an oil valve in an oil-filled vacuum-type on-load tap changer (OLTC), the gas sensor for monitoring a gas level in an oil within the oil valve; and a bi-level alarm system electrically connected with the gas sensor, the bi-level alarm system including a visual alarm indicator configured to provide a visual alarm in response to receiving an indication the gas level in the oil exceeds a threshold.

20 Claims, 1 Drawing Sheet

(56) References Cited

U.S. PATENT DOCUMENTS

| | | | |
|---|---|---|---|
| 5,271,263 | A | 12/1993 | Gibeault |
| 5,773,709 | A | 6/1998 | Gibeault et al. |
| 5,859,590 | A * | 1/1999 | Otani ............................ 340/635 |
| 6,242,711 | B1 * | 6/2001 | Cooper ..................... 219/130.01 |
| 6,401,518 | B1 | 6/2002 | O'Keeffe et al. |
| 6,446,027 | B1 | 9/2002 | O'Keeffe et al. |
| 6,494,617 | B1 | 12/2002 | Stokes et al. |
| 6,656,335 | B2 | 12/2003 | Babes-Dornea et al. |
| 7,582,196 | B2 | 9/2009 | Babes-Dornea et al. |
| 2006/0250683 | A1 | 11/2006 | Balan |
| 2007/0240438 | A1 | 10/2007 | King |
| 2008/0024945 | A1 * | 1/2008 | Gao et al. ......................... 361/42 |
| 2009/0255900 | A1 * | 10/2009 | Qin ................................. 216/64 |
| 2010/0040935 | A1 | 2/2010 | Babes-Dornea et al. |
| 2011/0246088 | A1 * | 10/2011 | Santos ............................. 702/24 |

OTHER PUBLICATIONS

Search Report and Written Opinion from corresponding EP Application No. 12168507.7-1232 dated Oct. 4, 2012.

GE Energy, "HYDRAN 2011 System Technical Specifications", pp. 1-16, Jun. 1, 2004.

GE Energy, "Kelman TRANSFIX" on-line DGA (Dissolved Gas Analysis) unit and moisture for transformers, pp. 1-2, Feb. 28, 2009.

GE Energy, "GE Digital Energy. Kelman TRANSFIX" on-line DGA (Dissolved Gas Analysis) unit and moisture for transformers, pp. 1-2, Aug. 31, 2010.

BPL Global, "Serveron TM TM3 On-line Transformer Monitor", pp. 1-6, Dec. 31, 2010.

General Electric, "GE Energy Expands Asset Monitoring Portfolio, Launches Cost-Effective, Warning Solution for Less Critical Transformers", pp. 1, Mar. 29, 2011.

GE Energy. "IntellixTM GLA 100. Cost Effective Transformer Warning Solution", pp. 1-2, Mar. 29, 2011.

General Electric, "GE Energy Expands Asset Monitoring Portfolio, Launches Cost-Effective. Warning Solution for Less Critical Transformers", pp. 1, Mar. 29, 2011.

GE Energy, "GE Energy Expands Asset Monitoring Portfolio. Launches Cost-Effective Warning Solution for Less Critical Transformers", pp. 1-4, Mar. 30, 2011.

Anonymous, "Warning Solution for Less Critical Transformers", pp. 1-4, May 1, 2011.

U.S. Appl. No. 13/112,424, filed May 20, 2011, Office Action dated Aug. 6, 2012.

Search Report issued in connection with EP Application No. 121658506.9, Oct. 9, 2012.

* cited by examiner

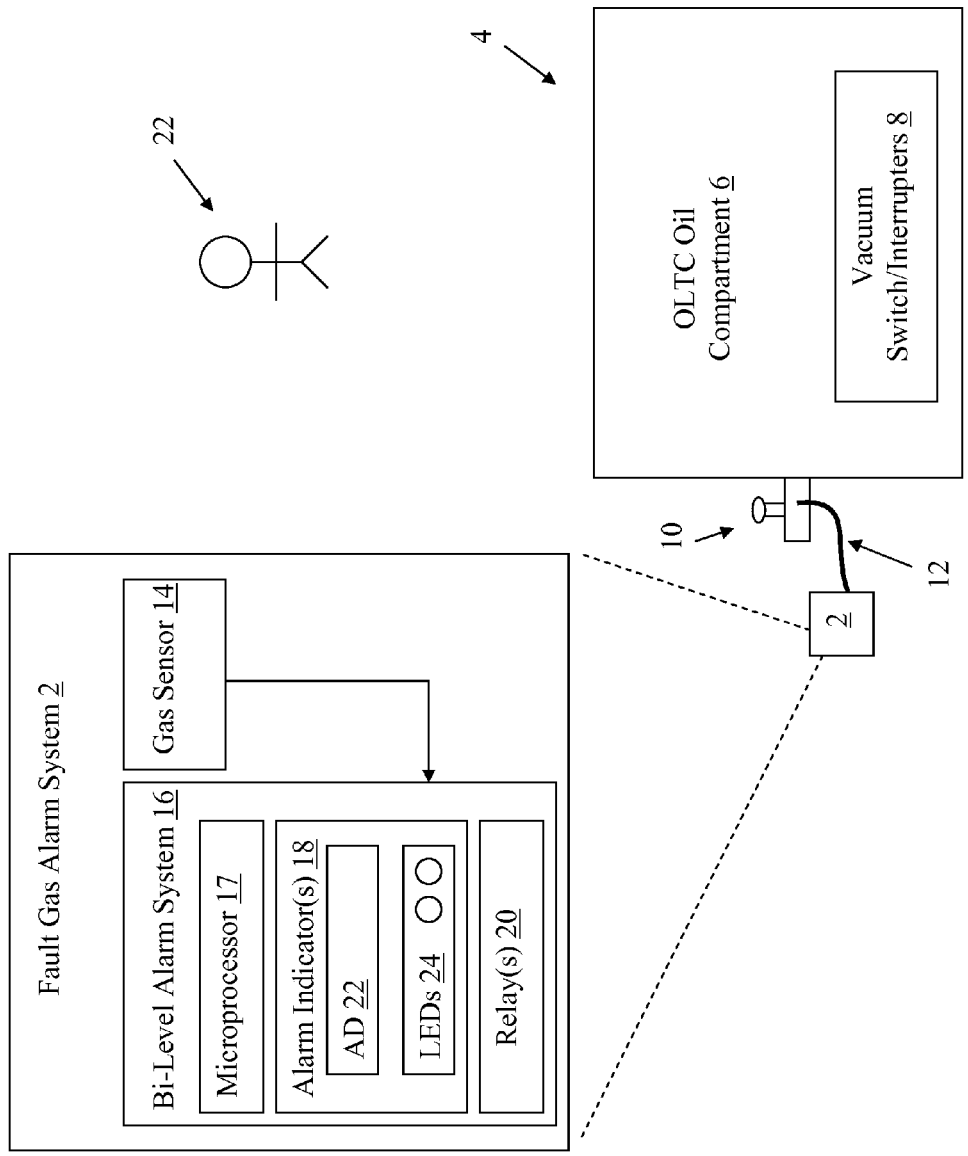

FAULT GAS ALARM SYSTEM

This application is related to concurrently filed U.S. patent application Ser. No. 13/112,424, now U.S. Pat. No. 8,405,991, entitled "HEAT TRANSFER ELEMENT TEMPERATURE VARIATION SYSTEM."

BACKGROUND OF THE INVENTION

The subject matter disclosed herein relates to on-load tap changers (OLTCs). Specifically, the subject matter disclosed herein relates to a fault gas alarm system for an oil-filled vacuum-type OLTC.

As is known in the art, an on-load tap changer (or, OLTC) is used to change the tapping connection of a transformer's winding while the transformer is energized. Various forms of OLTC devices exist in the art, however, aspects of the invention are directed toward oil-filled vacuum-type OLTC devices.

In these oil-filled vacuum-type OLTC devices, gas is not present in the vacuum during the normal (or, non-alarm) state. When gas (e.g., hydrogen and/or carbon monoxide) appears above trace levels in a vacuum-type OLTC, a problem typically exists. Current approaches used to monitor the presence of gas in oil-filled vacuum-type OLTC devices involve elaborate and expensive monitoring hardware, and are not specifically tailored for oil-filled vacuum-type OLTC devices.

BRIEF DESCRIPTION OF THE INVENTION

A fault gas alarm system is disclosed. In one embodiment, the fault gas alarm system includes: a gas sensor configured to fluidly connect with an oil valve in an oil-filled vacuum-type on-load tap changer (OLTC), the gas sensor for monitoring a gas level in an oil within the oil valve; and a bi-level alarm system electrically connected with the gas sensor, the bi-level alarm system including a visual alarm indicator configured to provide a visual alarm in response to receiving an indication the gas level in the oil exceeds a threshold.

A first aspect of the invention includes a fault gas alarm system having: a gas sensor configured to fluidly connect with an oil valve in an oil-filled vacuum-type on-load tap changer (OLTC), the gas sensor for monitoring a gas level in an oil within the oil valve; and a bi-level alarm system electrically connected with the gas sensor, the bi-level alarm system including: a visual alarm indicator configured to provide a visual alarm in response to receiving an indication the gas level in the oil exceeds a threshold.

A second aspect of the invention includes a fault gas alarm system having: a gas sensor configured to fluidly connect with an oil valve in an oil-filled vacuum-type on-load tap changer (OLTC), the gas sensor for monitoring a gas level in an oil within the oil valve; and a bi-level alarm system electrically connected with the gas sensor, the bi-level alarm system including a visual alarm indicator having two distinct light-emitting-diodes, wherein each of the two distinct light-emitting-diodes is configured to provide a distinct visual alarm in response to receiving an indication the gas level in the oil exceeds a threshold.

A third aspect of the invention includes a fault gas alarm system comprising: a gas sensor configured to fluidly connect with an oil conduit in an oil-filled vacuum-type on-load tap changer (OLTC), the gas sensor configured to monitor a gas level in an oil within the oil conduit; and a bi-level alarm system electrically connected with the gas sensor, the bi-level alarm system including: a microprocessor operably connected to the gas sensor; a visual alarm indicator having a light-emitting-diode operably connected to the microprocessor; and a direct contact relay operably connected to the microprocessor, the microprocessor for triggering the direct contact relay and the visual alarm indicator in response to receiving an indication the gas level in the oil exceeds a threshold.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 1 shows a schematic environment illustrating a fault gas alarm system and an on-load tap changer (OLTC) according to embodiments of the invention.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

The subject matter disclosed herein relates to an on-load tap changer (OLTC). Specifically, the subject matter disclosed herein relates to a fault gas alarm system for an oil-filled vacuum-type OLTC.

As is known in the art, an on-load tap changer (or, OLTC) is used to change the tapping connection of a transformer's winding while the transformer is energized. Various forms of OLTC devices exist in the art, however, aspects of the invention are directed toward oil-filled vacuum-type OLTC devices.

In these oil-filled vacuum-type OLTC devices, gas is not present in the vacuum during the normal (or, non-alarm) state. When gas (e.g., hydrogen and/or carbon monoxide) appears above trace levels in a vacuum-type OLTC, a problem typically exists. Current approaches used to monitor the presence of gas in oil-filled vacuum-type OLTC devices involve elaborate and expensive monitoring hardware, and are not specifically tailored for oil-filled vacuum-type OLTC devices.

In contrast to conventional approaches, aspects of the invention include a system having a gas sensor sensitive to particular gases (e.g., hydrogen and carbon monoxide), where the gas sensor is fluidly connected to an oil valve in the oil-filled vacuum-type OLTC device. The gas sensor may be configured to monitor an amount of gas present in the oil. The system further includes a bi-level alarm system (e.g., for "first" and "second" alarm levels). The bi-level alarm system may include a microprocessor, a relay (e.g., a direct contact relay) and an alarm indicator (e.g., a light-emitting diode). After receiving an indication that one or more alarm levels are reached, the microprocessor may trigger one or more relays and one or more alarm indicator(s), which may be in the form of a colored light-emitting diode (LED). In some cases, the first color LED may be yellow or orange, and the second may be red, purple, or black.

In one embodiment, aspects of the invention include: a fault gas alarm system having: a gas sensor configured to fluidly connect with an oil valve in an oil-filled vacuum-type on-load tap changer (OLTC), the gas sensor configured to monitor a gas level in an oil within the oil valve; and a bi-level alarm system electrically connected with the gas sensor, the bi-level alarm system including a visual alarm indicator configured to provide a visual alarm in response to receiving an indication the gas level in the oil exceeds a threshold.

Turning to FIG. 1, a schematic environment is shown including a blown-out view of a fault gas alarm system 2 in conjunction with an oil-filled on-load tap changer (OLTC) 4 according to embodiments of the invention. The blown-out view is illustrated using diverging dashed lines. As is known in the art, the OLTC 4 may include an OLTC oil compartment 6, tap and change-over selectors, vacuum switch or interrupters 8, by-pass switches, a drive mechanism/cam switch assembly, and other conventional accessories. As is further known in the art the OLTC oil compartment 6 may house a multi-phase (e.g., three-phase) selector. Further explanation of the vacuum compartment 8 is omitted herein for brevity. In any case, the OLTC 4 may include a valve 10 fluidly connected with the oil within the housing of the OLTC oil compartment 6, where the valve 10 is at least partially in contact with a flow of the oil within the OLTC oil compartment 6. It is understood that the valve 10 may be located within the housing of the OLTC oil compartment 6, or may be located externally, as depicted in FIG. 1. In either case, the valve 10 is fluidly connected with the oil within the housing of the OLTC oil compartment 6.

As shown, the fault gas alarm system 2 may be fluidly connected (e.g., via a conduit 12, such as a tube, hose, channel, etc. or via integral formation or placement) with the valve 10 such that the fault gas alarm system 2 has access to the oil within the valve 10. The fault gas alarm system 2 may include a gas sensor 14 configured to fluidly connect with the oil valve 10. The gas sensor 14 may be configured to monitor a gas level in the oil within the oil valve 10. In one embodiment, the gas sensor 14 may include a hydrogen detection sensor (e.g., a fuel cell sensor) configured to detect the presence of hydrogen in the oil within the oil valve 10. The gas sensor (e.g., hydrogen detection sensor) 14 may be a conventional fuel cell sensor configured to react to the presence of hydrogen at a predetermined level by closing an open fuel cell circuit, and thereby allowing a signal to pass through the fuel cell. In another embodiment, the gas sensor 14 may include a conventional carbon monoxide-sensing device configured to detect the presence of carbon monoxide within the oil inside oil valve 10. In another embodiment, the gas sensor 14 may include a combined hydrogen/carbon monoxide detection device for detecting an amount of one or both of hydrogen or carbon monoxide above a threshold amount. In another embodiment, one or more sensors included in the gas sensor 14 may be of a non-fuel cell type. For example, gas sensor 14 may include a first membrane (e.g., a polymeric membrane) in contact with the liquid (e.g., oil), and a second membrane in contact with ambient air.

The fault gas alarm system 2 may further include a bi-level alarm system 16 electrically connected (e.g., via hard-wired or wireless connection) with the gas sensor 14. The bi-level alarm system 16 may include a microprocessor 17 (e.g., a conventional microprocessor), an alarm indicator 18 and a relay 20, one or more of which may be operably connected to the gas sensor 14 (e.g., via the hard-wired or wireless connection). The relay 20 may be a conventional direct contact relay configured to trigger the alarm indicator 18 in response to receiving a command from the microprocessor 17, which in turn receives an indication that the gas level in the oil exceeds a threshold (via the gas sensor 14). More particularly, when the gas sensor 14 detects a gas (e.g., hydrogen or carbon monoxide) is present above a predetermined threshold amount in the oil within oil valve 10, the gas sensor 14 sends a signal to the microprocessor 17, which then triggers the relay 20 and indicators 18. In some cases, the threshold for the alarm (second level) and/or the caution (first level) may be user-settable. In some cases, the threshold for the alarm level may be between approximately 100 parts per million (ppm) and 5000 ppm, and the caution level (first level) may be set a percentage of the alarm level (e.g., approximately 40 percent to approximately 80 percent). In some cases, a default alarm level may be set at approximately 500 ppm.

After the gas sensor 14 sends the signal corresponding to a particular gas level (e.g., caution or alarm) to the microprocessor 17, the microprocessor 17 may trigger a corresponding relay 20 and alarm indicator 18 to change status, where the corresponding alarm indicator 18 may become illuminated (or, flash) to signal an alarm event. The microprocessor 17 is configured to trigger the alarm indicator 18 and the relay(s) 20 in response to processing that the gas level in the oil exceeds a threshold, based upon the sensor reading. In some embodiments, the predetermined threshold is set at approximately 500 ppm for the alarm level and approximately 400 ppm for the caution level.

In any case, the alarm indicator 18 may be configured to signal at least one alarm in response to receiving the relayed signal from the relay 20. The alarm indicator 18 may include at least one of a visual and/or audible alarm. For example, the alarm indicator 18 may include a speaker, siren or other acoustic device (AD) 22 configured to create an audible noise in response to receiving the signal from the relay 20. As noted, the bi-level alarm system 16 may include an alarm having two levels. In this case, the alarm indicator 18 may include a first alarm level and a second alarm level. In some embodiments, the alarm indicator 18 may include a preliminary or "warning" alarm indicating a first concentration of gas detected by the gas sensor 14, and a subsequent or "severe" alarm indicating a second, greater concentration of the gas detected by the gas sensor 14. In some cases, the second, more severe alarm indicator is configured to draw greater attention from an observer (e.g., a human operator 22). For example, the second alarm may be louder and/or higher pitched in the case of an audible alarm, or may be brighter or of a higher frequency in the case of a visual alarm (e.g., a light). In some embodiments, the alarm indicator includes one or more light-emitting diodes (LEDs) 24, where the LEDs 24 have distinct colors (which may indicate distinct alarm severities). In some cases, the first alarm LED 24 may be yellow or orange, and the second alarm LED 24 may be red, black or purple.

In any case, the fault gas alarm system 2 disclosed according to embodiments of the invention may be configured to alert an operator (e.g., a human operator 22) that a gas level in the oil valve 10 exceeds a predetermined threshold. The fault gas alarm system 2 disclosed according to embodiments of the invention may provide a simple, cost-effective solution for fault gas sensing in an oil-filled vacuum-type OLTC device as compared with conventional systems and approaches. That is, when compared to conventional approaches, minimal hardware components can be implemented in the fault gas alarm system 2, while still providing an effective gas alarm function in an oil-filled vacuum-type OLTC device.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A fault gas alarm system comprising:
    a gas sensor configured to fluidly connect with an oil valve in an oil-filled vacuum-type on-load tap changer (OLTC), the gas sensor for monitoring a gas level in an oil within the oil valve; and
    a bi-level alarm system electrically connected with the gas sensor, the bi-level alarm system including a visual alarm indicator configured to provide a visual alarm in response to receiving an indication the gas level in the oil exceeds a threshold.

2. The fault gas alarm system of claim 1, wherein the alarm indicator includes two distinct alarm levels.

3. The fault gas alarm system of claim 1, wherein the alarm indicator includes a first light-emitting-diode.

4. The fault gas alarm system of claim 3, wherein the alarm indicator includes a second light-emitting diode having a color distinct from the first light-emitting diode.

5. The fault gas alarm system of claim 1, wherein the bi-level alarm system has access to the oil within the valve, and wherein the oil valve is in contact with a flow of the oil within an oil compartment of the OLTC.

6. The fault gas alarm system of claim 1, wherein the bi-level alarm system further includes:
    a microprocessor operably connected to the gas sensor; and
    a relay operably connected to the microprocessor, wherein the microprocessor is configured to trigger the relay and the visual alarm indicator in response to receiving the indication the gas level in the oil exceeds the threshold.

7. The fault gas alarm system of claim 1, wherein the gas includes one of hydrogen or carbon monoxide.

8. The fault gas alarm system of claim 1, wherein the gas sensor is a fuel cell type gas sensor.

9. A fault gas alarm system comprising:
    a gas sensor configured to fluidly connect with an oil valve in an oil-filled vacuum-type on-load tap changer (OLTC), the gas sensor for monitoring a gas level in an oil within the oil valve; and
    a bi-level alarm system electrically connected with the gas sensor, the bi-level alarm system including a visual alarm indicator having two distinct light-emitting-diodes, wherein each of the two distinct light-emitting-diodes is configured to provide a distinct visual alarm in response to receiving an indication the gas level in the oil exceeds a threshold.

10. The fault gas alarm system of claim 9, wherein the two distinct light-emitting diodes include distinct color indicators.

11. The fault gas alarm system of claim 9, wherein the bi-level alarm system further includes:
    a microprocessor operably connected to the gas sensor; and
    a relay operably connected to the microprocessor, wherein the microprocessor is configured to trigger the relay and the visual alarm indicator in response to receiving the indication the gas level in the oil exceeds the threshold.

12. The fault gas alarm system of claim 9, wherein the bi-level alarm system further includes an audible alarm.

13. The fault gas alarm system of claim 9, wherein the gas includes hydrogen.

14. The fault gas alarm system of claim 9, wherein the gas includes carbon monoxide.

15. The fault gas alarm system of claim 9, wherein the gas sensor is a fuel cell type gas sensor.

16. The fault gas alarm system of claim 9, wherein the bi-level alarm system has access to the oil within the valve, and wherein the oil valve is in contact with a flow of the oil within an oil compartment of the OLTC.

17. A fault gas alarm system comprising:
    a gas sensor configured to fluidly connect with an oil conduit in an oil-filled vacuum-type on-load tap changer (OLTC), the gas sensor for monitoring a gas level in an oil within the oil conduit; and
    a bi-level alarm system electrically connected with the gas sensor, the bi-level alarm system including:
        a microprocessor operably connected to the gas sensor;
        a visual alarm indicator having a light-emitting-diode operably connected to the microprocessor; and
        a direct contact relay operably connected to the microprocessor, the microprocessor for triggering the direct contact relay and the visual alarm indicator in response to receiving a signal that the gas level in the oil exceeds a threshold.

18. The fault gas alarm system of claim 17, wherein the gas sensor is a fuel cell type gas sensor.

19. The fault gas alarm system of claim 17, wherein the gas includes one of hydrogen and carbon monoxide.

20. The fault gas alarm system of claim 17, wherein the bi-level alarm system has access to the oil within the valve, and wherein the oil valve is in contact with a flow of the oil within an oil compartment of the OLTC.

* * * * *